United States Patent
Yoshida (10) Patent No.: US 10,774,115 B2
(45) Date of Patent: Sep. 15, 2020

(54) MODIFIED FAB REGION-BINDING PEPTIDE

(71) Applicant: Kaneka Corporation, Osaka (JP)

(72) Inventor: Shinichi Yoshida, Hyogo (JP)

(73) Assignee: KANEKA CORPORATION, Osaka (JP)

(*) Notice: Subject to any disclaimer, the term of this patent is extended or adjusted under 35 U.S.C. 154(b) by 130 days.

(21) Appl. No.: 15/686,666

(22) Filed: Aug. 25, 2017

(65) Prior Publication Data

US 2017/0355733 A1    Dec. 14, 2017

Related U.S. Application Data (63) Continuation of application No. PCT/JP2016/055701, filed on Feb. 25, 2016.

(30) Foreign Application Priority Data

Feb. 26, 2015  (JP) ................ 2015-036424

(51) Int. Cl.
| | | |
|---|---|---|
| C07K 14/31 | (2006.01) | |
| C07K 14/315 | (2006.01) | |
| C12N 15/09 | (2006.01) | |
| G01N 30/88 | (2006.01) | |
| C07K 16/24 | (2006.01) | |
| A61K 39/44 | (2006.01) | |
| A61K 38/00 | (2006.01) | |
| A61K 39/00 | (2006.01) | |
| C07K 19/00 | (2006.01) | |
| B01J 20/289 | (2006.01) | |
| B01J 20/32 | (2006.01) | |
| B01D 15/38 | (2006.01) | |

(52) U.S. Cl.
CPC .............. *C07K 14/31* (2013.01); *A61K 39/44* (2013.01); *B01J 20/289* (2013.01); *B01J 20/321* (2013.01); *B01J 20/3212* (2013.01); *B01J 20/3219* (2013.01); *B01J 20/3274* (2013.01); *C07K 14/315* (2013.01); *C07K 16/241* (2013.01); *C12N 15/09* (2013.01); *G01N 30/88* (2013.01); *A61K 38/00* (2013.01); *A61K 2039/505* (2013.01); *B01D 15/3809* (2013.01); *C07K 19/00* (2013.01); *C07K 2317/55* (2013.01); *C07K 2317/732* (2013.01); *C07K 2317/92* (2013.01); *C07K 2319/23* (2013.01); *C07K 2319/50* (2013.01)

(58) Field of Classification Search
None
See application file for complete search history.

(56) References Cited

U.S. PATENT DOCUMENTS

| | | |
|---|---|---|
| 5,756,670 A | 5/1998 | Guss et al. |
| 5,976,861 A | 11/1999 | Guss et al. |
| 2015/0183820 A1* | 7/2015 | Honda ............... C07K 17/14 |
| | | 210/198.2 |
| 2016/0289306 A1 | 10/2016 | Yoshida et al. |

FOREIGN PATENT DOCUMENTS

| | | |
|---|---|---|
| JP | S63503032 A | 11/1988 |
| JP | 2009195184 A | 9/2009 |
| JP | 2009297018 A | 12/2009 |
| JP | 2015003872 A | 1/2015 |
| WO | 2014021240 A1 | 2/2014 |
| WO | 2015030094 A1 | 3/2015 |

OTHER PUBLICATIONS

International Search Report issued in International Application No. PCT/JP2016/055701; dated May 24, 2016 (2 pages).
Hober et al.; "Protein A chromatography for antibody purification" Journal of Chromatography B, 848 (2007) 40-47 (8 pages).
Shukla et al.; "Recent advances in large-scale production of monoclonal antibodies and related proteins" Trends in Biotechnology, vol. 28, No. 5, Mar. 19, 2010, pp. 253-261 (9 pages).
Nelson et al.; "Development trends for therapeutic antibody fragments" Nature Biotechnology, vol. 27, No. 4, Apr. 2009, pp. 331-337 (7 pages).
Bouvet; "Immunoglobulin Fab Fragment-Binding Proteins" Int. J. Immunopharmac., vol. 16, No. 5/6, 1994, pp. 419-424 (6 pages).
Derrick et al.; "Crystal structure of a streptococcal protein G domain bound to an Fab fragment" Letters to Nature, vol. 359, Oct. 22, 1992, pp. 752-754 (3 pages).
Bailey et al.; "Applications for an engineered Protein-G variant with a pH controllable affinity to antibody fragments" Journal of Immunological Methods, vol. 415, 2014, pp. 24-30 (7 pages).
Watanabe et al.; "Optimizing pH Response of Affinity between Protein G and IgG Fc" The Journal of Biological Chemistry, vol. 284, No. 18, May 1, 2009, pp. 12373-12383 (12 pages).

* cited by examiner

*Primary Examiner* — Patricia Duffy
(74) *Attorney, Agent, or Firm* — Osha Liang LLP

(57) ABSTRACT

A first Fab region-binding peptide includes an amino acid sequence selected from the group consisting of SEQ ID NOs: 1 to 5 with substitution of one or more amino acid residues at the 17$^{th}$ position and the 36$^{th}$ position, wherein an acid dissociation pH thereof is shifted to a neutral side. A second Fab region-binding peptide further includes deletion, substitution and/or addition of one or more amino acid residues at positions other than the 17$^{th}$ position and the 36$^{th}$ position. A third Fab region-binding peptide includes an amino acid sequence with a sequence identity of 80% or more to the amino acid sequence of the first Fab region-binding peptide.

6 Claims, 2 Drawing Sheets
Specification includes a Sequence Listing.

SEQUENCE LISTING

<160> NUMBER OF SEQ ID NOS: 20

<210> SEQ ID NO 1
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 1

Thr Thr Tyr Lys Leu Ile Leu Asn Gly Lys Thr Leu Thr Gly Tyr Thr
1               5                   10                  15

Thr Ala Ile Ala Ala Asp Ala Ala Thr Ala Glu Ile Val Leu Lys Gln
            20                  25                  30

Phe Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 2
<211> LENGTH: 56
<212> TYPE: PRT
<213> ORGANISM: Artificial Sequence
<220> FEATURE:
<223> OTHER INFORMATION: SpG-beta1-mutant

<400> SEQUENCE: 2

Thr Thr Tyr Lys Leu Ile Leu Asn Gly Lys Thr Leu Thr Gly Tyr Thr
1               5                   10                  15

Thr Thr Ile Ala Val Asp Ala Ala Thr Ala Glu Lys Val Leu Lys Gln
            20                  25                  30

Phe Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 3
<211> LENGTH: 56
<212> TYPE: PRT
<213> ORGANISM: Streptococcus mutans

<400> SEQUENCE: 3

Thr Thr Tyr Lys Leu Ile Leu Asn Gly Lys Thr Leu Lys Gly Glu Thr
1               5                   10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 4
<211> LENGTH: 56
<212> TYPE: PRT
<213> ORGANISM: Streptococcus mutans

<400> SEQUENCE: 4

Thr Thr Tyr Lys Leu Val Ile Asn Gly Lys Thr Leu Lys Gly Glu Thr
1               5                   10                  15

Thr Thr Lys Ala Val Asp Ala Glu Thr Ala Glu Lys Ala Phe Lys Gln
                20                  25                  30

Tyr Ala Asn Asp Asn Gly Val Asp Gly Val Trp Thr Tyr Asp Asp Ala
            35                  40                  45

Thr Lys Thr Phe Thr Val Thr Glu
    50                  55

<210> SEQ ID NO 5
<211> LENGTH: 56
<212> TYPE: PRT
<213> ORGANISM: Artificial Sequence
<220> FEATURE:
<223> OTHER INFORMATION: SpG-beta2-mutant

<400> SEQUENCE: 5

Thr Thr Tyr Lys Leu Val Ile Asn Gly Lys Thr Leu Lys Gly Glu Thr
1               5                   10                  15

Thr Thr Lys Ala Val Asp Ala Glu Thr Ala Glu Arg Ala Phe Arg Gln
                20                  25                  30

Tyr Ala Thr Asp Asn Gly Val Glu Gly Met Trp Thr Tyr Asp Pro Ala
            35                  40                  45

Thr Lys Thr Phe Thr Val Thr Glu
    50                  55

<210> SEQ ID NO 6
<211> LENGTH: 171
<212> TYPE: DNA
<213> ORGANISM: Artificial Sequence
<220> FEATURE:
<223> OTHER INFORMATION: Immunoglobulin-binding peptide code DNA

<400> SEQUENCE: 6
accacctaca aactgatcct gaacggtaag accctgacag gttacaccac cgccatagct    60
gctgacgctg ctacggccga aattgtgctc aaacagttcg ctaacgacaa cggtatcgac   120
ggtgaatgga cctacgacga cgctaccaaa accttcacgg ttaccgaata a            171

<210> SEQ ID NO 7
<211> LENGTH: 57
<212> TYPE: DNA
<213> ORGANISM: Artificial Sequence
<220> FEATURE:
<223> OTHER INFORMATION: Primer

<400> SEQUENCE: 7
cgtggatcca ccacctacaa actgatcctg aacggtaaga ccctgacagg ttacacc       57

<210> SEQ ID NO 8
<211> LENGTH: 45
<212> TYPE: DNA
<213> ORGANISM: Artificial Sequence
<220> FEATURE:
<223> OTHER INFORMATION: Primer

<400> SEQUENCE: 8
aatttcggcc gtagcagcgt cagcagctat ggcggtggtg taacc                     45

<210> SEQ ID NO 9
<211> LENGTH: 60

```
<212> TYPE: DNA
<213> ORGANISM: Artificial Sequence
<220> FEATURE:
<223> OTHER INFORMATION: Primer

<400> SEQUENCE: 9
gctacggccg aaattgtgct caaacagttc gctaacgaca acggtatcga cggtgaatgg      60

<210> SEQ ID NO 10
<211> LENGTH: 60
<212> TYPE: DNA
<213> ORGANISM: Artificial Sequence
<220> FEATURE:
<223> OTHER INFORMATION: Primer

<400> SEQUENCE: 10
gatgaattct tattcggtaa ccgtgaaggt tttggtagcg tcgtcgtagg tccattcacc      60

<210> SEQ ID NO 11
<211> LENGTH: 68
<212> TYPE: DNA
<213> ORGANISM: Artificial Sequence
<220> FEATURE:
<223> OTHER INFORMATION: Primer

<400> SEQUENCE: 11
cgtggatcca ccacctacaa actgatcctg aacggtaaga ccctgacagg ttacaccgcc      60
gccatagc                                                              68

<210> SEQ ID NO 12
<211> LENGTH: 68
<212> TYPE: DNA
<213> ORGANISM: Artificial Sequence
<220> FEATURE:
<223> OTHER INFORMATION: Primer

<400> SEQUENCE: 12
cgtggatcca ccacctacaa actgatcctg aacggtaaga ccctgacagg ttacaccgtc      60
gccatagc                                                              68

<210> SEQ ID NO 13
<211> LENGTH: 60
<212> TYPE: DNA
<213> ORGANISM: Artificial Sequence
<220> FEATURE:
<223> OTHER INFORMATION: Primer

<400> SEQUENCE: 13
gctacggccg aaattgtgct caaacagttc gctaacgtca acggtatcga cggtgaatgg      60

<210> SEQ ID NO 14
<211> LENGTH: 171
<212> TYPE: DNA
<213> ORGANISM: Artificial Sequence
<220> FEATURE:
<223> OTHER INFORMATION: GB1#-mutant cDNA

<400> SEQUENCE: 14
accacctaca aactgatcct gaacggtaag accctgacag gttacaccgc cgccatagct      60
gctgacgctg ctacggccga aattgtgctc aaacagttcg ctaacgacaa cggtatcgac     120
ggtgaatgga cctacgacga cgctaccaaa accttcacgg ttaccgaata a              171

<210> SEQ ID NO 15
```

<211> LENGTH: 171
<212> TYPE: DNA
<213> ORGANISM: Artificial Sequence
<220> FEATURE:
<223> OTHER INFORMATION: GB1#-mutant cDNA

<400> SEQUENCE: 15
accacctaca aactgatcct gaacggtaag accctgacag gttacaccgt cgccatagct      60
gctgacgctg ctacggccga aattgtgctc aaacagttcg ctaacgacaa cggtatcgac     120
ggtgaatgga cctacgacga cgctaccaaa accttcacgg ttaccgaata a              171

<210> SEQ ID NO 16
<211> LENGTH: 171
<212> TYPE: DNA
<213> ORGANISM: Artificial Sequence
<220> FEATURE:
<223> OTHER INFORMATION: GB1#-mutant cDNA

<400> SEQUENCE: 16
accacctaca aactgatcct gaacggtaag accctgacag gttacaccac cgccatagct      60
gctgacgctg ctacggccga aattgtgctc aaacagttcg ctaacgtcaa cggtatcgac     120
ggtgaatgga cctacgacga cgctaccaaa accttcacgg ttaccgaata a              171

<210> SEQ ID NO 17
<211> LENGTH: 56
<212> TYPE: PRT
<213> ORGANISM: Artificial Sequence
<220> FEATURE:
<223> OTHER INFORMATION: GB1#-mutant

<400> SEQUENCE: 17

Thr Thr Tyr Lys Leu Ile Leu Asn Gly Lys Thr Leu Thr Gly Tyr Thr
1               5                   10                  15

Ala Ala Ile Ala Ala Asp Ala Ala Thr Ala Glu Ile Val Leu Lys Gln
            20                  25                  30

Phe Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 18
<211> LENGTH: 56
<212> TYPE: PRT
<213> ORGANISM: Artificial Sequence
<220> FEATURE:
<223> OTHER INFORMATION: GB1#-mutant

<400> SEQUENCE: 18

Thr Thr Tyr Lys Leu Ile Leu Asn Gly Lys Thr Leu Thr Gly Tyr Thr
1               5                   10                  15

Val Ala Ile Ala Ala Asp Ala Ala Thr Ala Glu Ile Val Leu Lys Gln
            20                  25                  30

Phe Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 19
<211> LENGTH: 56
<212> TYPE: PRT
<213> ORGANISM: Artificial Sequence

```
<220> FEATURE:
<223> OTHER INFORMATION: GB1#-mutant

<400> SEQUENCE: 19

Thr Thr Tyr Lys Leu Ile Leu Asn Gly Lys Thr Leu Thr Gly Tyr Thr
1               5                   10                  15

Thr Ala Ile Ala Ala Asp Ala Ala Thr Ala Glu Ile Val Leu Lys Gln
                20                  25                  30

Phe Ala Asn Val Asn Gly Ile Asp Gly Glu Trp Thr Tyr Asp Asp Ala
        35                  40                  45

Thr Lys Thr Phe Thr Val Thr Glu
    50                  55

<210> SEQ ID NO 20
<211> LENGTH: 5
<212> TYPE: PRT
<213> ORGANISM: Artificial Sequence
<220> FEATURE:
<223> OTHER INFORMATION: derived from vector pGEX-6P-1

<400> SEQUENCE: 20

Gly Pro Leu Gly Ser
1               5
```

MODIFIED FAB REGION-BINDING PEPTIDE

CROSS-REFERENCE TO RELATED APPLICATIONS

This application is a continuation of International Patent Application No. PCT/JP2016/055701, filed on Feb. 26, 2016, which claims priority to Japanese Patent Application No. 2015-036424, filed on Feb. 26, 2015. The contents of the priority applications are incorporated by reference in their entirety.

TECHNICAL FIELD

One or more embodiments of the present invention relate to a modified Fab region-binding peptide which binds to a Fab region of IgG and which dissociates a Fab region in a milder acidic condition, an affinity separation matrix containing the modified Fab region-binding peptide as a ligand, a method for producing a Fab region-containing protein by using the affinity separation matrix, a DNA encoding the modified Fab region-binding peptide, a vector containing the DNA, and a transformant which is transformed by the vector.

BACKGROUND

As one of important functions of a protein, a capability to specifically bind to a specific molecule is exemplified. The function plays an important role in an immunoreaction and signal transduction in a living body. A technology utilizing the function for purifying a useful substance has been actively developed. As one example of proteins which are actually utilized industrially, for example, Protein A affinity separation matrix has been used for capturing an antibody drug to be purified with high purity at one time from a culture of an animal cell (Non-patent documents 1 and 2). Hereinafter, Protein A is abbreviated as "SpA" in some cases.

An antibody drug which has been developed is mainly a monoclonal antibody, and a monoclonal antibody has been produced on a large scale by using recombinant cell cultivation technology. A "monoclonal antibody" means an antibody obtained from a clone derived from a single antibody-producing cell. Most of antibody drugs launched presently are classified into an immunoglobulin G (IgG) in terms of a molecular structure. In addition, an antibody drug consisting of an antibody fragment has been actively subjected to clinical development. An antibody fragment is an antibody derivative having a molecular structure obtained by fragmenting IgG. A plurality of antibody drugs consisting of a Fab fragment of an immunoglobulin has been clinically developed (Non-patent Document 3).

In an initial purification step of an antibody drug production, the above-described SpA affinity separation matrix is utilized. SpA is however basically a protein which specifically binds to a Fc region of IgG. Thus, SpA affinity separation matrix cannot capture an antibody fragment which does not contain a Fc region. Accordingly, an affinity separation matrix capable of capturing an antibody fragment which does not contain a Fc region of IgG is highly required industrially in terms of a platform development of a process for purifying an antibody drug.

A plurality of peptides which can bind to a region except for a Fc region of IgG have been already known (Non-patent Document 4). There is however no fact that an affinity separation matrix having such a protein as a ligand is industrially used for purifying an antibody drug in a general way similarly to SpA affinity separation matrix.

For example, Protein G found from *Streptococcus* sp. classified in Group G binds to IgG. Hereinafter, Protein G is abbreviated as "SpG" in some cases. A SpG affinity separation matrix product on which SpG is immobilized as a ligand is commercially available (Product name: "Protein-G Sepharose 4 Fast Flow" manufactured by GE Healthcare, Patent Document 1). SpG strongly binds to a Fc region of IgG, and it has been known that SpG weakly binds to a Fab region (Non-patent Documents 4 and 5). It is however considered that a SpG affinity separation matrix product has low capability of adsorbing an antibody fragment containing a Fab region only and not containing a Fc region, since a binding capability of SpG to a Fab region is not strong. Accordingly, a binding capability of SpG to a Fab region has been tried to be improved by introducing a mutation to SpG (Patent Document 2 and Non-patent Document 6).

A ligand used for an affinity separation matrix product is needed not only to have a strong binding capability to a target molecule but also to dissociate the binding in an appropriate condition to recover the target molecule adsorbed on the matrix. A protein such as SpG dissociates IgG in an acidic condition. An interaction between SpG and Fab is lost surely in a lower pH condition; however, when the pH is lower, Fab suffers damage such as a chemical modification and a cleavage. It is therefore preferred to perform a dissociation in a pH condition closer to neutrality as much as possible. For example, it has been known that the pH to dissociate Fc is shifted to somewhat neutrality side (Patent Document 3 and Non-patent Document 7) and the pH to dissociate Fab is shifted to somewhat neutrality side (Non-patent Document 6) by introducing a substitution mutation to His in SpG, since the pKa of a histidine side chain is about pH 6. The position to be mutated and the kind of an amino acid to be mutated should be however studied in the future, since an intermediate washing is sometimes performed at about pH 5, which is closer to neutrality than the pKa of His, in a chromatography procedure using an affinity separation matrix.

Patent Document 1: JP S63-503032 T
Patent Document 2: JP 2009-195184 A
Patent Document 3: JP 2009-297018 A
Non-patent Document 1: Hober S., et al., J. Chromatogr. B, 2007, vol. 848, pp. 40-47
Non-patent Document 2: Shukla A. A., et al., Trends Biotechnol., 2010, vol. 28, pp. 253-261
Non-patent Document 3: Nelson A. N., et al., Nat. Biotechnol., 2009, vol. 27, pp. 331-337
Non-patent Document 4: Bouvet P. J., et al., Int. J. Immunopharmac., 1994, vol. 16, pp. 419-424
Non-patent Document 5: Derrick J. P., et al., Nature, 1992, vol. 359, pp. 752-754
Non-patent Document 6: Bailey L. J., et al., J. Immunol. Methods, 2014, vol. 415, pp. 24-30
Non-patent Document 7: Watanabe H., et al., J. Biol. Chem., 2009, vol. 284, pp. 12373-12383

As described above, various affinity separation matrixes to purify an immunoglobulin or a fragment thereof have been developed. In general, in order to purify an immunoglobulin or a fragment thereof by an affinity separation matrix, a neutral solution is contacted with an affinity separation matrix to selectively adsorb the immunoglobulin or fragment thereof, the matrix is washed to remove an impurity, and then the adsorbed immunoglobulin or fragment thereof is eluted by using an acidic eluate. In such a process, in order to obtain a target compound with high purity, it is needed to use an affinity separation matrix with high selective adsorbability and to sufficiently perform washing. In addition, in order to obtain a target compound with high collection rate, it is needed to conduct an elution in the range of acidic pH by which a selective adsorption can be certainly dissociated. However, an immunoglobulin or a fragment thereof as a target compound may suffer damage in a strong acidic condition.

The inventor has found in the past that it is needed to enhance the capability of wild Protein G (SpG) to Fab as a ligand of an affinity separation matrix, since the binding capability of SpG to Fab is weaker than the binding capability to Fc (Patent Document 2). In addition, it has been also found that the pH to dissociate Fab is sometimes shifted to stronger acidic side, in other words, an acid dissociation pH value is sometimes decreased, by enhancing a binding capability of SpG to Fab by a mutation in comparison with a dissociation pH before the introduction of the mutation.

SUMMARY

One or more embodiments of the present invention provide a modified Fab region-binding peptide which has an excellent selective adsorbability to a Fab region of IgG but which can release an adsorbed Fab region-containing protein by an acidic eluate with relatively high pH. Also, one or more embodiments of the present invention provide an affinity separation matrix containing the modified Fab region-binding peptide as a ligand, a method for producing a Fab region-containing protein by using the affinity separation matrix, a DNA encoding the modified Fab region-binding peptide, a vector containing the DNA, and a transformant which is transformed by the vector.

The inventor designed a molecular of a modified IgG-binding domain of SpG, prepared the mutant from a transformant using a protein engineering means and a genetic engineering means, and compared the properties of the prepared mutants. As a result, the inventor completed one or more embodiments of the present invention by introducing a specific mutation into a IgG-binding domain of SpG.

Specifically, the inventor identified a position which has an effect on an acid dissociation pH but which does not seriously damage a binding capability to Fab by using the following molecular calculatory chemistry procedure.

The structural coordinate of the crystal structure of the complex of a IgG-binding domain of SpG and a Fab region of IgG (Derrick J. P. and Wigley D. B., J. Mol. Biol., 1994, vol. 243, pp. 906-918) was obtained from PDB (Protein Data Bank, PDB code of the coordinate: 1IGC) to be selected as a form coordinate for a molecular modeling. Then, a molecular modeling was performed to fit the IgG-binding domain in the crystal structure to the amino acid sequence of β1 domain of SpG (SEQ ID NO: 1) by using a three-dimensional graphics program such as Swiss-PDBViewer (Guex N., et al., Electrophoresis, 1997, vol. 18, pp. 2714-2733) so that the obtained modeling structure is used for comparison. Next, with respect to various amino acid sequences of a modified IgG binding-domain of SpG, a similar procedure was performed. A stability of a protein can be evaluated by a structural energy (A. R. Leach, "MOLECULAR MODELING—PRINCIPLES AND APPLICATIONS—", 2004, Chapter 11). A structural energy of a complex of a IgG-binding domain of SpG and a Fab region of IgG can be calculated by using a molecular modeling structure, in other words, a framework of a main chain, and by molecular simulation calculation to minimize energy due to molecular force field method. Accordingly, an effect by a mutation can be evaluated by using a stability of a protein complex as an indicator and by comparing structural energies of each modeling structure before and after the mutation. Specifically, an effect by a mutation was evaluated by changing parameter relevant to a permittivity of a solvent and by comparing some of the calculation results to minimize an energy (force field parameter: CHARMM, main α carbon position bondage: 0.01 kcal/A) using program Shrike (JP 2001-184381 A).

As a result, the inventor found that the $17^{th}$ position and the $36^{th}$ position of a IgG-binding domain of SpG are appropriate for a mutation. The $17^{th}$ position is located far away from an interfacial surface of the domain and CH1 of Fab. It was surprisingly suggested that a mutation at the $17^{th}$ position has an effect on a stability of a protein complex depending on a solvent condition without severely impairing a binding capability to Fab. In addition, the $36^{th}$ position is located at an interfacial surface of the domains and CL of Fab. The interfacial surface area thereof is narrower than that of CH1; however, it was surprisingly suggested that a mutation at the $36^{th}$ position has an effect on a stability of a protein complex depending on a solvent condition without severely impairing a binding capability to Fab.

Hereinafter, one or more embodiments of the present invention completed by the above-described study are described.

[1] A modified Fab region-binding peptide, being any one of the following (1) to (3):

(1) a Fab region-binding peptide having an amino acid sequence corresponding to any one of amino acid sequences of SEQ ID NOs: 1 to 5 with substitution of one or more amino acid residues at positions selected from the group consisting of the $17^{th}$ position and the $36^{th}$ position ("first Fab region-binding peptide"), wherein an acid dissociation pH thereof is shifted to a neutral side in comparison with an acid dissociation pH before introducing the substitution;

(2) a Fab region-binding peptide having an amino acid sequence specified in the (1) with a mutation of deletion, substitution and/or addition of 1 or some amino acid residues in a region except for the $17^{th}$ position and the $36^{th}$ position ("second Fab region-binding peptide"), wherein an acid dissociation pH thereof is shifted to a neutral side in comparison with an acid dissociation pH before introducing the mutation;

(3) a Fab region-binding peptide having an amino acid sequence with a sequence identity of 80% or more to the amino acid sequence specified in the (1) ("third Fab region-binding peptide"), wherein an acid dissociation pH thereof is shifted to a neutral side in comparison with an acid dissociation pH before introducing the mutation, provided that the amino acid residue substitution specified in the (1) at one or more positions selected from the group consisting of the $17^{th}$ position and the $36^{th}$ position is not further mutated in (3).

[2] The modified Fab region-binding peptide according to the above [1], wherein the amino acid residue at the $17^{th}$ position is substituted in the amino acid sequence specified in the (1).

[3] The modified Fab region-binding peptide according to the above [1] or [2], wherein the $17^{th}$ position is substituted by Ala, Val, Ser, Leu or Ile in the amino acid sequence specified in the (1).

[4] The modified Fab region-binding peptide according to any one of the above [1] to [3], wherein the $36^{th}$ position is substituted by Ala, Val, Thr or Glu in the amino acid sequence specified in the (1).

[5] The modified Fab region-binding peptide according to any one of the above [1] to [4], wherein a position of the mutation is one or more positions selected from the group consisting of the $6^{th}$ position, the $7^{th}$ position, the $10^{th}$ position, the $13^{th}$ position, the $15^{th}$ position, the $18^{th}$ position, the $19^{th}$ position, the $21^{st}$ position, the $24^{th}$ position, the $28^{th}$ position, the $29^{th}$ position, the $30^{th}$ position, the $31^{st}$ position, the $33^{rd}$ position, the $35^{th}$ position, the $37^{th}$ position, the $39^{th}$ position, the $40^{th}$ position, the $42^{nd}$ position and the $47^{th}$ position in the amino acid sequence specified in the (2).

[6] The modified Fab region-binding peptide according to any one of the above [1] to [5], wherein a position of the mutation is N-terminal and/or C-terminal in the amino acid sequence specified in the (2).

[7] A modified Fab region-binding peptide multimer, comprising two or more domains formed by connecting two or more of the modified Fab region-binding peptides according to any one of the above [1] to [6].

[8] An affinity separation matrix, wherein the modified Fab region-binding peptide according to any one of the above [1] to [6] or the modified Fab region-binding peptide multimer according to the above [7] is immobilized on a water-insoluble carrier as a ligand.

[9] A method for producing a protein comprising a Fab region, comprising the steps of:
  contacting the affinity separation matrix according to the above [8] with a liquid sample comprising the protein comprising the Fab region; and
  separating the protein comprising the Fab region bound on the affinity separation matrix from the affinity separation matrix.

[10] A DNA, encoding the modified Fab region-binding peptide according to any one of the above [1] to [6].

[11] A vector, comprising the DNA according to the above [10].

[12] A transformant, transformed by the vector according to the above [11].

The affinity separation matrix prepared by immobilizing the modified Fab region-binding peptide according to one or more embodiments of the present invention on an insoluble carrier has excellent selective adsorbability to a Fab region-containing protein. On the one hand, the affinity separation matrix also has an excellent acid dissociation property as a conflicting property. The term "excellent acid dissociation property" means that a Fab region-containing protein is dissociated in an acidic condition closer to neutrality for elution and an elution peak profile when a Fab region-containing protein is eluted in an acidic condition is sharper. When an elution peak of chromatography is sharper, an eluate which contains an antibody with high concentration and of which volume is smaller can be obtained.

DETAILED DESCRIPTION OF THE EMBODIMENTS

The modified Fab region-binding peptide according to one or more embodiments of the present invention is characterized in being any one of the following (1) to (3):

(1) a Fab region-binding peptide having an amino acid sequence corresponding to any one of amino acid sequences of SEQ ID NOs: 1 to 5 with substitution of one or more amino acid residues at positions selected from the group consisting of the $17^{th}$ position and the $36^{th}$ position ("first Fab region-binding peptide"), wherein an acid dissociation pH thereof is shifted to a neutral side in comparison with an acid dissociation pH before introducing the substitution;

(2) a Fab region-binding peptide having an amino acid sequence specified in the (1) with a mutation of deletion, substitution and/or addition of 1 or some amino acid residues in a region except for the $17^{th}$ position and the $36^{th}$ position ("second Fab region-binding peptide"), wherein an acid dissociation pH thereof is shifted to a neutral side in comparison with an acid dissociation pH before introducing the mutation;

(3) a Fab region-binding peptide having an amino acid sequence with a sequence identity of 80% or more to the amino acid sequence specified in the (1) ("third Fab region-binding peptide"), wherein an acid dissociation pH thereof is shifted to a neutral side in comparison with an acid dissociation pH before introducing the mutation, provided that the amino acid residue substitution specified in the (1) at one or more positions selected from the group consisting of the $17^{th}$ position and the $36^{th}$ position is not further mutated in (3).

An "immunoglobulin (IgG)" is a glycoprotein produced by a B cell of a lymphocyte and has a function to recognize a specific molecule such as a protein to be bound. An immunoglobulin has not only a function to specifically bind to a specific molecule referred to as antigen but also a function to detoxify and remove an antigen-containing factor in cooperation with other biological molecule or cell. An immunoglobulin is generally referred to as "antibody", and the name is inspired by such functions. All of immunoglobulins basically have the same molecular structure. The basic structure of an immunoglobulin is a Y-shaped four-chain structure consisting of two light chains and two heavy chains of polypeptide chains. A light chain (L chain) is classified into two types of λ chain and κ chain, and all of immunoglobulins have either of the chains. A heavy chain (H chain) is classified into five types of γ chain, μ chain, α chain, δ chain and ε chain, and an immunoglobulin is classified into isotypes depending on the kind of a heavy chain. An immunoglobulin G (IgG) is a monomer immunoglobulin, is composed of two heavy chains (γ chains) and two light chains, and has two antigen-binding sites.

A lower half vertical part in the "Y" shape of an immunoglobulin is referred to as a "Fc region", and an upper half "V" shaped part is referred to as a "Fab region". A Fc region has an effector function to initiate a reaction after an antibody binds to an antigen, and a Fab region has a function to bind to an antigen. A Fab region of a heavy chain and Fc region are bound to each other through a hinge part. Papain, which is a proteolytic enzyme and which is contained in papaya, decomposes a hinge part to cut into two Fab regions and one Fc region. The domain part close to the tip of the "Y" shape in a Fab region is referred to as a "variable region (V region)", since there are various changes of the amino acid sequence in order to bind to various antigens. A variable region of a light chain is referred to as a "VL region", and a variable region of a heavy chain is referred to as a "VH region". A Fab region except for a V region and a Fc region are referred to as a "constant region (C region)", since there is relatively less change. A constant region of a light chain is referred to as a "CL region", and a constant region of a heavy chain is referred to as a "CH region". A CH region is further classified into three regions of CH1 to CH3. A Fab region of a heavy chain is composed of a VH region and CH1, and a Fc region of a heavy chain is composed of CH2 and CH3. There is a hinge part between CH1 and CH2. More specifically, SpG-β binds to CH1 region (CH1γ) and CL region of IgG, particularly to CH1 region mainly (Non-patent Document 5).

The modified Fab region-binding peptide according to one or more embodiments of the present invention binds to a Fab region of an immunoglobulin. A Fab region-containing protein to which the peptide according to one or more embodiments of the present invention binds is not particularly restricted as long as the protein contains a Fab region, and may be an immunoglobulin molecule containing both of a Fab region and a Fc region or an immunoglobulin molecule derivative. Such an immunoglobulin molecule derivative to be bound by the modified Fab region-binding peptide according to one or more embodiments of the present invention is not particularly restricted as long as the derivative contains a Fab region. The derivative is exemplified by a Fab fragment which is fragmented to only a Fab region of an immunoglobulin G, a chimera immunoglobulin G prepared by replacing a part of domains of a human immunoglobulin G with a domain of an immunoglobulin G derived from other organism to be fused, an immunoglobulin G of which a sugar chain in a Fc region is subjected to molecular alteration, and a Fab fragment to which a drug covalently binds.

The term "peptide" in one or more embodiments of the present invention means any molecules having a polypeptide structure. In the range of the "peptide", not only a so-called protein but also a fragmented peptide and a peptide to which other peptide is bound through a peptide bond are included. The term "domain" means a unit of higher-order structure of a protein. A domain is composed of from dozens to hundreds of amino acid residues, and means a peptide unit which can sufficiently serve some kind of a physicochemical or biochemical function. The term "modified protein or peptide" means a protein or peptide obtained by introducing at least one substitution, addition or deletion of an amino acid into a sequence of a wild protein or peptide. A mutation to substitute an amino acid is described by adding a wild or non-mutated amino acid residue before the number of a substituted position and adding a mutated amino acid residue after the number of the substituted position. For example, the mutation to substitute Thr at $17^{th}$ position by Val is described as T17V.

Protein G (SpG) is a protein derived from a cell wall of *Streptococcus* sp. classified in Group G. SpG has a capability to bind to an immunoglobulin G (IgG) of most mammals, strongly binds to a Fc region of IgG and weakly binds to a Fab region of IgG.

The functional domain having a binding capability to IgG in SpG is referred to as β domain (SpG-β). The domain is referred to as β (B) domain or C domain (refer to Akerstrom et al., J. Biol. Chem., 1987, 28, p. 13388-, FIG. 5), but is referred to as "β domain" in the present disclosure in accordance with the definition of Fahnestock et al. (Fahnestock et al., J. Bacteriol., 1986, 167, p. 870-).

The amino acid sequence specified in the above-described modified Fab region-binding peptide (1) basically has the structure and function as SpG-β. As the above-described modified Fab region-binding peptide (1), a modified SpG-β having an improved binding capability to Fab, such as a further modified SpG-β mutant having the amino acid sequence of any one of SEQ ID NOs: 1 to 5, may be used.

In one or more embodiments of the present invention, the amino acid sequence of SEQ ID NO: 2 of a modified SpG-β having an improved binding capability to Fab may be among the amino acid sequences of SEQ ID NOs: 1 to 5 specified in the above-described (1). In addition, wild SpG-β may be utilized in one or more embodiments of the present invention. In one or more embodiments of the present invention, the amino acid sequences of β1 domain (SpG-β1, SEQ ID NO: 3) and β2 domain (SpG-β2, SEQ ID NO: 4) derived from *Streptococcus* sp. GX7809 strain classified in Group G may be among the amino acid sequences of SEQ ID NOs: 1 to 5 specified in the above-described (1). In one or more embodiments of the present invention, the amino acid sequence of SEQ ID NO: 5 described in JP 2003-88381 of a modified SpG-β having excellent thermal stability is exemplified. The amino acid sequence corresponds to the amino acid sequence of SEQ ID NO: 8 described in JP 2003-88381 of C36 peptide. The amino acid residue at the N-terminal/C-terminal of the amino acid sequences of SEQ ID NOs: 1 to 5 may be mutated for experimental reasons.

In one or more embodiments of the present invention, the specific substitution mutation is introduced in one of the amino acid sequences of SEQ ID NO: 1 to 5; as a result, the pH to dissociate a protein containing a Fab region by an acid is shifted to a neutral side in comparison with that before the introduction of the mutation. The specific substitution mutation of the amino acid in the Fab region-binding peptide (1) of one or more embodiments of the present invention is a mutation to substitute one or more amino acid residues selected from the group consisting of the amino acid residues at the $17^{th}$ position and the $36^{th}$ position by other amino acid, and the amino acid sequence before the introduction of the mutation or the introduction of the substitution is the amino acid sequence of SEQ ID NO: 1. For example, when the substitution specified in the above-described (1) is T17A only, an amino acid sequence obtained by introducing A17T as a reverse mutation in the amino acid sequence of the peptide is the amino acid sequence before the introduction of the mutation.

As experimentally demonstrated in Examples described later, the modified Fab region-binding peptide (1) of one or more embodiments of the present invention dissociates a Fab region-containing protein in an acidic condition for elution with higher pH; and when a Fab region-containing protein is eluted in an acidic condition, an elution peak is sharper.

The amino acid sequence before the introduction of the mutation of the modified Fab region-binding peptide (1) of one or more embodiments of the present invention may be any one of the amino acid sequences of SEQ ID NOs: 1 to 5, the amino acid sequence of SEQ ID NO: 1 or SEQ ID NO: 2, or the amino acid sequence of SEQ ID NO: 1, but is not restricted thereto.

The modified Fab region-binding peptide (1) of one or more embodiments of the present invention has the amino acid sequence of which one or more amino acid residues at a position selected from the group consisting of the $17^{th}$ position and the $36^{th}$ position is substituted. The position to be substituted may be the $17^{th}$ position. In the amino acid sequences of SEQ ID NOs: 1 to 5, the $17^{th}$ position may be Thr and the $36^{th}$ position may be Asp.

The phrase, a peptide "has a (specific) amino acid sequence", in one or more embodiments of the present invention means that the specific amino acid sequence is contained in the amino acid sequence of the peptide and the function of the peptide is maintained. The sequence of the peptide other than the specific amino acid sequence is exemplified by histidine tag, a linker sequence for immobilization, and a crosslinking structure such as —S—S— bond.

Even when a peptide is added to the N-terminal, a skilled person can easily identify a position corresponding to the $17^{th}$ position and the $36^{th}$ position in the amino acid sequences of SEQ ID NOs: 1 to 5 with reference to a sequence identity. For example, such a position can be identified by using the alignment function of gene information processing software: GENETYX.

The kind of the amino acid after the mutation, in other words, the kind of the amino acid which substitutes for Thr at the $17^{th}$ position and/or Asp at the $36^{th}$ position in the amino acid sequences of SEQ ID NOs: 1 to 5 is not particularly restricted, the mutation may be a substitution by a non-protein-constituting amino acid and a non-natural amino acid, and a natural amino acid may be used in terms of genetic engineering production. A natural amino acid is classified into the categories of a neutral amino acid; an acidic amino acid such as Asp and Glu; and a basic amino acid such as Lys, Arg and His. A neutral amino acid is classified into the categories of an aliphatic amino acid; an imino acid such as Pro; and an aromatic amino acid such as Phe, Tyr and Trp. An aliphatic amino acid is classified into the categories of Gly; Ala; a branched amino acid such as Val, Leu and Ile; a hydroxy amino acid such as Ser and Thr; a sulfur-containing amino acid such as Cys and Met; and an acid amide amino acid such as Asn and Gln. Since Tyr has a phenolic hydroxyl group, Tyr may be classified into not only an aromatic amino acid but also a hydroxy amino acid. From another viewpoint, a natural amino acid may also be classified into the categories of a nonpolar amino acid with high hydrophobicity, such as Gly, Ala, Val, Leu, Ile, Trp, Cys, Met, Pro and Phe; a neutral polar amino acid such as Asn, Gln, Ser, Thr and Tyr; an acidic polar amino acid such as Asp and Glu; and a basic polar amino acid such as Lys, Arg and His. In addition, His, Asp and Glu may be used, since the amino acids has a functional group in a side chain, which group can be protonated in an acidic condition.

The amino acid which substitutes for the amino acid at the $17^{th}$ position may be Ala, Val, Ser, Leu or Ile, Ala or Val, or Val. The amino acid which substitutes for the amino acid at the $36^{th}$ position may be Ala, Val, Thr or Glu, Ala, Val or Thr, or Val. From another perspective, the amino acid which substitutes for the amino acids at the $17^{th}$ position and the $36^{th}$ position may not be Gly, since Gly may destabilize a β-sheet structure.

The Fab region-binding peptide (2) of one or more embodiments of the present invention has an amino acid sequence specified in the above-described (1) with a mutation of deletion, substitution and/or addition of 1 or some amino acid residues in a region except for the $17^{th}$ position and the $36^{th}$ position, and an acid dissociation pH thereof is shifted to a neutral side in comparison with an acid dissociation pH before introducing the mutation.

The range of "1 or some" in the modified Fab region-binding peptide (2) of one or more embodiments of the present invention is not particularly restricted as long as the modified Fab region-binding peptide having the deletion, substitution and/or addition has strong binding capability to a Fab region of an immunoglobulin. The range of "1 or some" may be 30 or less, 20 or less, 10 or less, 7 or less, 5 or less, 3 or less, 1 or 2, or 1.

The position of the 1 or more mutations may be any positions as long as the position is not the $17^{th}$ position and the $36^{th}$ position. For example, the position of the mutation may be the $10^{th}$ position, the $13^{th}$ position, the $15^{th}$ position, the $18^{th}$ position, the $19^{th}$ position, the $21^{st}$ position, the $28^{th}$ position, the $30^{th}$ position, the $31^{st}$ position, the $33^{rd}$ position or the $39^{th}$ position at which the amino acids are different between SEQ ID NOs: 1 to 3. In addition, the position of the mutation may be the $6^{th}$ position, the $7^{th}$ position, the $19^{th}$ position, the $24^{th}$ position, the $28^{th}$ position, the $29^{th}$ position, the $31^{st}$ position, the $35^{th}$ position, the $40^{th}$ position, the $42^{nd}$ position or the $47^{th}$ position at which the amino acids are different between SEQ ID NOs: 3 to 5.

The position of the deletion, substitution and/or addition of the amino acid residue may be exemplified by N-terminal and/or C-terminal. The terminal positions may be as the position of the deletion and/or addition. In one or more embodiments of the present invention in which an amino acid sequence is added, an amino acid sequence containing Lys or Cys, which are useful for immobilizing the peptide on a matrix, may be added to the C-terminal portion.

Even when the number of amino acids is changed by the above-described deletion or addition, the position of an amino acid residue after introducing the mutation which position corresponds to the position of an amino acid residue before introducing the mutation can be easily identified by alignment analysis between the amino acid sequences before and after introducing the mutation. The means of such an alignment analysis is widely known by a person skilled in the art as the explanation with respect to the modified Fab region-binding peptide (1).

The sequence identity specified in the modified Fab region-binding peptide (3) of one or more embodiments of the present invention may be 80% or more, 85% or more, 90% or more, 95% or more, or 98% or more. The sequence identity can be evaluated by a program for amino acid sequence multiple alignment, such as Clustal, as the explanation with respect to the modified Fab region-binding peptide (1).

The one or more substituted amino acid residues at the position selected from the group consisting of the $17^{th}$ position and the $36^{th}$ position in the amino acid sequence specified in the above-described (1) is not further mutated in (3). Even when the numbers of amino acids in the amino acid sequences before and after the introduction of the mutation are different, a skilled person can easily identify a position corresponding to the $17^{th}$ position and the $36^{th}$ position of SEQ ID NOs: 1 to 5 under the condition that the sequence identity is 80% or more.

The Fab region-binding peptides (1) to (3) according to one or more embodiments of the present invention are characterized in that the pH to dissociate a Fab region-containing protein by an acid is shifted to a neutral side in comparison with an acid dissociation pH before the introduction of the substitution or the mutation. In general, the connection between peptides is lost in a strong acidic condition and a strong basic condition by the change of the charge on a molecular surface and the change of a steric structure due to a denaturation. The term "acid dissociation pH" means a pH at which the specific connection is lost at an acid side, i.e. when a pH value is less than 7, leading to dissociation. In other words, the acid dissociation pH means the highest pH to dissociate and elute an adsorbed Fab region-containing protein from an affinity separation matrix having the Fab region-binding peptides (1) to (3) according to one or more embodiments of the present invention as a ligand. In the present disclosure, an acid dissociation pH and an acid elution pH basically have the same meaning. The phrase "an acid dissociation pH is shifted to a neutral side in comparison with an acid dissociation pH before the introduction of the substitution or the mutation" means that the value of the pH necessary for dissociation of the connection is smaller before the introduction of the substitution or the mutation and larger after the introduction of the substitution or the mutation. In other words, the connection can be dissociated by using a weaker acidic solution after the introduction of the substitution or the mutation.

It is difficult to unambiguously determine the value range of the acid dissociation pH, since the value is changed depending on the kind of a Fab region-containing protein, the kind and concentration of a buffer component in an acidic solution; and with respect to an affinity separation matrix, the value is also changed depending on the kind and structure of a water-insoluble carrier and the kind and structure of a linker for immobilizing a ligand. In general, the acid dissociation pH before introducing the mutation is about 2.0 or more and about 3.5 or less; on the one hand, the pH after introducing the mutation according to one or more embodiments of the present invention is not restricted but is shifted to about 3.0 or more and about 4.5 or less, but is not restricted thereto. When an elution is carried out in such a condition, the adsorbed antibody can be eluted with less damage (chose S., et al., Biotechnology and bioengineering, 2005, vol. 92, no. 6). When the mutation according to one or more embodiments of the present invention is introduced, the acid dissociation pH may be shifted to the neutral side by 0.1 or more, or the pH may be shifted to the neutral side by 0.2 or more, or the pH may be shifted to the neutral side by 0.3 or more, or the pH may be shifted to the neutral side by 0.4 or more, or the pH may be shifted to the neutral side by 0.5 or more.

The method for measuring the acid dissociation pH before and after introducing the mutation is not restricted as long as the interaction between biomolecules can be evaluated by the method. For example, the pH can be measured by a biosensor such as Biacore system (GE Healthcare) utilizing a surface plasmon resonance principle. As a method for measuring the acid dissociation pH, for example, one peptide or protein to be interacted is immobilized on a sensor tip, a solution of another peptide or protein having an adjusted pH is added into a flow channel, it is evaluated whether a binding signal is detected or not, and the pH at which a binding signal is not detected is specified; but the method is not restricted thereto. As another method, a buffer solution having an adjusted pH is added after adding a peptide solution or protein solution, and then a change of binding signals due to the remaining peptide or protein without dissociation before and after the addition may be evaluated. With respect to a measurement condition, a temperature is kept constant in a range between 20 and 40° C. and the pH is adjusted to be neutral between 5 and 8 when a binding condition is observed. A component of a buffer solution is exemplified by phosphoric acid, tris(hydroxymethyl)aminomethane, bis[tris(hydroxymethyl)aminomethane] in the case of a neutral buffer, and by acetic acid, citric acid and glycine in the case of an acidic buffer, but is not restricted thereto. The concentration of NaCl in a buffer solution is not particularly restricted, and may be about 0 to 0.15 M, or may be 0 M when a dissociation condition is observed. In the above-described evaluation, it is important to equalize the conditions other than the mutation in order to compare the difference before and after the mutation. For example, when Biacore system is used for the evaluation, the Fab region-binding peptide may be immobilized on a chip as a solid phase or may be added in a flow channel as a liquid phase, and the evaluation is possible in both cases. For example, when it is difficult to adjust the amount of the Fab region-binding peptide to be constant, the Fab region-binding peptide may be added to the flow channel with adjusting the concentration to be added to the flow channel to be constant.

As a method for evaluating the acid dissociation pH, a method for evaluating a chromatography profile with using an affinity separation matrix may be used. For example, one peptide or protein to be bound is immobilized on a column for chromatography, the column is connected to a chromatography device, a solution of another protein or peptide is added into the column, pH of an eluent is gradually reduced with a linear gradient to elute the adsorbed protein or peptide, and the pH corresponding to the top peak of the eluted peptide is specified, but the method is not restricted thereto. The temperature, buffer and salt concentration during the measurement may be adjusted as the above, but are not restricted thereto. For example, the components of a buffer A for association and a buffer B for dissociation may be the same other than pH for clear linear gradient. It is important in the measurement to equalize all of the conditions except for the mutation in order to compare the difference before and after the mutation. Also, in the evaluation method, the Fab region-binding peptide may be immobilized on a column as a solid phase or may be added to be eluted as a liquid phase, and the evaluation is possible in both cases. For example, when it is difficult to adjust the amount of the Fab region-binding peptide which is immobilized on a column, the concentration of the Fab region-binding peptide to be added into the column may be adjusted and the obtained chromatography profiles may be overlapped to be compared.

Protein G is a protein which contains 2 or 3 immunoglobulin-binding domains in the form of tandem line. As one or more of the embodiments, the modified Fab region-binding peptide of one or more embodiments of the present invention may be a multimer of 2 or more monomers or single domains of the modified Fab region-binding peptide connected each other. The number of the monomers or single domains may be 3 or more, 4 or more, or 5 or more. With respect to the upper limit of the number of connected domains, the number may be 10 or less, 8 or less, or 6 or less. Such a multimer may be a homomultimer in which one kind of modified Fab region-binding peptides are connected, such as homodimer and homotrimer, or a heteromultimer in which two or more kinds of Fab region-binding peptides are connected, such as heterodimer and heterotrimer.

A method for connecting the modified Fab region-binding peptide of one or more embodiments of the present invention is exemplified by a connecting method through one or more amino acid residues and a directly connecting method without an amino acid residue, but is not restricted thereto. The number of the amino acid residue for connection is not particularly restricted, and may be 1 residue or more and 20 residues or less, 15 residues or less, 10 residues or less, 5 residues or less, or 2 residues or less. The sequence which connect β1 and β2 or β2 and β3 of wild SpG may be used. From another perspective, The amino acid residue for connection may not destabilize a three dimensional structure of the modified Fab region-binding peptide monomer.

The modified Fab region-binding peptide of one or more embodiments of the present invention has the amino acid sequence specified in the modified Fab region-binding peptides (1) to (3) and may be further bound to other peptide and compound. For example, a fusion peptide characterized in that the modified Fab region-binding peptide of one or more embodiments of the present invention or a multimer formed by connecting two or more the peptides as one component may be fused with other peptide having a different function is exemplified. A fusion peptide may be a peptide fused with albumin or GST, i.e. glutathione S-transferase, but is not restricted to the examples. In addition, peptides fused with a nucleic acid such as DNA aptamer, a drug such as an antibiotic or a polymer such as PEG, i.e. polyethylene glycol, are also included in the range of one or more embodiments of the present invention as long as the availability of the peptide of one or more embodiments of the present invention is utilized in such a fusion peptide.

The modified Fab region-binding peptides (1) to (3) of one or more embodiments of the present invention can be immobilized on a column as an affinity ligand and have an excellent binding capability to Fab. For example, an affinity for a Fab region can be evaluated by a biosensor such as Biacore system using a surface plasmon resonance principle, but the means is not restricted thereto.

A binding parameter is exemplified by an affinity constant ($K_A$) and a dissociation constant ($K_D$) (Nagata et al., "Real-time analysis experiment of biomaterial interactions", Springer-Verlag Tokyo, 1998, page 41). The affinity constant corresponds to a value obtained by dividing a binding rate constant ($k_{on}$) by a dissociation rate constant ($k_{off}$), in other words, $K_A = k_{on}/k_{off}$.

For example, an affinity constant between the modified Fab region-binding peptide of one or more embodiments of the present invention and a Fab region-containing peptide can be measured by using Biacore system, specifically by immobilizing the Fab region-containing peptide on a sensor tip and adding the modified Fab region-binding peptide of one or more embodiments of the present invention to be flown into a channel in the conditions of 25° C. and pH 7.4. An affinity constant $K_A$ between the peptide having the mutated sequence according to one or more embodiments of the present invention and a Fab region-containing peptide may be $1 \times 10^5$ $M^{-1}$ or more, or $5 \times 10^5 M^{-1}$ or more; however, such an affinity constant is not restricted to the above-described values, since an affinity constant is varied depending on the kind of a Fab region-containing peptide and the number of domains in the Fab region-binding peptide.

It is included in one or more embodiments of the present invention that the peptide may be used as an affinity ligand which is characterized in having an affinity for an immunoglobulin or a fragment thereof, particularly a Fab region. An affinity separation matrix obtained by immobilizing the ligand on a water-insoluble carrier is also similarly included in one or more embodiments of the present invention. The term "affinity ligand" in the present disclosure means a substance and a functional group to selectively bind to or adsorb a target molecule from an aggregate of molecules on the basis of a specific affinity between molecules, such as interaction between an antigen and an antibody, and means the peptide which specifically binds to an immunoglobulin in one or more embodiments of the present invention. The term "ligand" in one or more embodiments of the present invention also means an "affinity ligand".

A water-insoluble carrier usable in one or more embodiments of the present invention is exemplified by an inorganic carrier such as glass beads and silica gel; an organic carrier; and a composite carrier obtained by the combination of the above carriers, such as an organic-organic composite carrier and an organic-inorganic composite carrier. An organic carrier is exemplified by a carrier composed of a synthetic polymer such as cross-linked polyvinyl alcohol, cross-linked polyacrylate, cross-linked polyacrylamide and cross-linked polystyrene; and a carrier composed of a polysaccharide such as crystalline cellulose, cross-linked cellulose, cross-linked agarose and cross-linked dextran. The commercial product thereof is exemplified by porous cellulose gel GCL2000, Sephacryl S-1000 prepared by crosslinking allyl dextran and methylene bisacrylamide through a covalent bond, an acrylate carrier Toyopearl, a cross-linked agarose carrier Sepharose CL4B, and a cross-linked cellulose carrier Cellufine. It should be noted, however, that the water-insoluble carrier usable in one or more embodiments of the present invention is not restricted to the carriers exemplified as the above.

The water-insoluble carrier usable in one or more embodiments of the present invention may have large surface area and that the carrier may be porous with a large number of fine pores having a suitable size in terms of a purpose and method for using the affinity separation matrix according to one or more embodiments of the present invention. The carrier may have any form such as beads, monolith, fiber and film (including hollow fiber), and any form can be selected.

With respect to a method for immobilizing the ligand, for example, the ligand can be bound to a carrier by a conventional coupling method utilizing an amino group, a carboxy group or a thiol group of the ligand. Such a coupling method is exemplified by an immobilization method including activation of a carrier by a reaction with cyanogen bromide, epichlorohydrin, diglycidyl ether, tosyl chloride, tresyl chloride, hydrazine, sodium periodate or the like, or introduction of a reactive functional group on the carrier surface, and the coupling reaction between the resulting carrier and a compound to be immobilized as a ligand; and an immobilization method by condensation and crosslinking which method includes adding a condensation reagent such as carbodiimide or a reagent having a plurality of functional groups in the molecule, such as glutaraldehyde, into a mixture containing a carrier and a compound to be immobilized as a ligand.

A spacer molecule composed of a plurality of atoms may be introduced between the ligand and carrier. Alternatively, the ligand may be directly immobilized on the carrier. Accordingly, the modified Fab region-binding peptide of one or more embodiments of the present invention may be chemically modified for immobilization, or may have an additional amino acid residue useful for immobilization. Such an amino acid useful for immobilization is exemplified by an amino acid having a functional group useful for a chemical reaction for immobilization in a side chain, and specifically exemplified by Lys having an amino group in a side chain and Cys having a thiol group in a side chain. Since the binding capability of one or more embodiments of the present invention peptide to a Fab region is principally maintained in a matrix prepared by immobilizing the peptide as a ligand in one or more embodiments of the present invention, any modification and change for immobilization are included in the range of one or more embodiments of the present invention.

It becomes possible by using the affinity separation matrix of one or more embodiments of the present invention that a protein containing a Fab region of an immunoglobulin is purified in accordance with affinity column chromatography purification method. A protein containing a Fab region of an immunoglobulin G can be purified by a procedure in accordance with a method for purifying an immunoglobulin by affinity column chromatography, for example, such as a method using SpA affinity separation matrix (Non-Patent Document 1). Specifically, after a buffer solution which contains an immunoglobulin G Fab region-containing protein and of which pH is approximately neutral is prepared, the solution is allowed to pass through an affinity column packed with the affinity separation matrix of one or more embodiments of the present invention so that the immunoglobulin G Fab region-containing protein is adsorbed. Then, an appropriate amount of a pure buffer is allowed to pass through the affinity column to wash the inside of the column. At the time, the target immunoglobulin G Fab region-containing protein is still adsorbed on the affinity separation matrix of one or more embodiments of the present invention in the column. The affinity separation matrix on which the peptide is immobilized as a ligand is excellent in the absorption and retention performance of a target immunoglobulin G Fab region-containing protein from the step of adding a sample through the step of washing the matrix. Then, an acid buffer of which pH is appropriately adjusted is allowed to pass through the column to elute the target immunoglobulin G Fab region-containing protein. As a result, purification with high purity can be achieved. Into the acid buffer used for eluting the peptide, a substance for promoting dissociation from the matrix may be added.

In particular, when the affinity separation matrix of one or more embodiments of the present invention is used, an acid buffer of which pH is closer to neutrality can be used as an eluate. The pH value of the acid buffer to be used may be 3.0 or more, 3.1 or more, 3.2 or more, 3.3 or more, 3.4 or more, 3.5 or more, 3.6 or more, 3.7 or more, or 3.8 or more. The upper limit of the pH value of an acid buffer to be used is not particularly restricted; and when intermediate washing is performed during an affinity chromatography using a washing solution having a pH of about 5.0 and an incubation is carried out at a pH of about 3.8 to remove virus after the purification, the pH value of an acid buffer to be used may be 4.5 or less, or 4.0 or less.

The affinity separation matrix of one or more embodiments of the present invention can be reused by allowing an adequate strong acid or strong alkaline pure buffer which do not completely impair the function of the ligand compound or the base material of the carrier to pass through the matrix for washing. In the buffer for reuse, an adequate modifying agent or an organic solvent may be added.

The affinity separation matrix of one or more embodiments of the present invention can be reused by allowing an adequate strong acid or strong alkaline pure buffer which do not completely impair the function of the ligand compound or the base material of the carrier to pass through the matrix for washing. In the buffer, an adequate modifying agent or an organic solvent may be added.

One or more embodiments of the present invention also relates to a DNA encoding the above-described modified Fab region-binding peptide of one or more embodiments of the present invention. The DNA encoding the peptide of one or more embodiments of the present invention may be any DNA as long as the amino acid sequence produced from translation of the base sequence of the DNA constitutes the peptide. Such a base sequence can be obtained by a common known method, for example, using polymerase chain reaction (hereinafter, abbreviated as "PCR") method. Alternatively, such abase sequence can be synthesized by a publicly-known chemical synthesis method or is available from a DNA library. A codon in the base sequence may be substituted by a degenerate codon, and the base sequence is not necessarily the same as the original base sequence as long as the translated amino acids are the same as those encoded by the original base sequence. It is possible to obtain a recombinant DNA having the one or more base sequences, a vector containing the recombinant DNA, such as a plasmid or a phage, a transformant which is transformed by the vector having the DNA, a genetically engineered organisms having the DNA introduced therein, or a cell-free protein synthesis system using the DNA as a template for transcription.

The modified Fab region-binding peptide of one or more embodiments of the present invention may be obtained as a fusion peptide fused with a publicly-known protein which beneficially has an action to assist the expression of the protein or to facilitate the purification of the protein. In other words, it is possible to obtain a microorganism or cell containing at least one recombinant DNA encoding a fusion peptide containing the modified Fab region-binding peptide of one or more embodiments of the present invention. The above-described protein is exemplified by a maltose-binding protein (MBP) and a glutathione S-transferase (GST), but is not restricted to the exemplified proteins.

Site-specific mutagenesis for modifying the DNA encoding the peptide of one or more embodiments of the present invention can be carried out using recombinant DNA technology, PCR method or the like as follows. For example, a mutagenesis by recombinant DNA technology can be carried out as follows: in the case where there are suitable restriction enzyme recognition sequences on both sides of a target mutagenesis site in the gene encoding the peptide, cassette mutagenesis method can be carried out in which method a region containing the target mutagenesis site is removed by cleaving the restriction enzyme recognition sites with the above-described restriction enzymes and then a mutated DNA fragment is inserted. Into the mutated DNA fragment, mutation is introduced only at the target site by a method such as chemical synthesis.

For example, site-directed mutagenesis by PCR can be carried out by double primer mutagenesis. In double primer mutagenesis, PCR is carried out by using a double-stranded plasmid encoding the peptide as a template, and using two kinds of synthesized oligo primers which contain complementary mutations in the + strand and − strand. A DNA encoding a multimer peptide can be produced by ligating the desired number of DNAs each encoding the monomer peptide (single domain) of one or more embodiments of the present invention to one another in tandem. For example, with respect to a method for connecting DNAs encoding the multimer peptide, a suitable restriction enzyme site is introduced in the DNA sequence and double-stranded DNA fragments cleaved with a restriction enzyme are ligated using a DNA ligase. One restriction enzyme site may be introduced or a plurality of restriction enzyme sites of different types may be introduced. When the base sequences encoding each monomer peptide in the DNA encoding the multimer peptide are the same, homologous recombination may be possibly induced in a host. Thus, the sequence identity between base sequences of DNAs encoding the monomer peptides to be connected may be 90% or less, 85% or less, 80% or less, or 75% or less. The sequence identity of a base sequence can be also determined by an ordinary method similarly to an amino acid sequence.

The "expression vector" of one or more embodiments of the present invention includes a base sequence encoding the above-described peptide of one or more embodiments of the present invention or a part of the amino acid sequence of the peptide, and a promoter that can be operably linked to the base sequence to function in a host. Usually, the vector can be constructed by linking or inserting a gene encoding the peptide of one or more embodiments of the present invention to a suitable vector. The vector for insertion of the gene is not particularly restricted as long as the vector is capable of autonomous replication in a host. As such a vector, a plasmid DNA or a phage DNA can be used. For example, in the case of using *Escherichia coli* as a host, a pQE series vector (manufactured by QIAGEN), a pET series vector (manufactured by Merck), a pGEX series vector (manufactured by GE Healthcare Bioscience) or the like can be used.

The transformant of one or more embodiments of the present invention can be produced by introducing the recombinant vector of one or more embodiments of the present invention into a host cell. A method for introducing the recombinant DNA into a host is exemplified by a method using a calcium ion, electroporation method, spheroplast method, lithium acetate method, agrobacterium infection method, particle gun method and polyethylene-glycol method, but is not restricted thereto. A method for expressing the function of the obtained gene in a host is also exemplified by a method in which the gene according to one or more embodiments of the present invention is implanted into a genome (chromosome). A host cell is not particularly restricted, and bacteria (eubacteria) such as *Escherichia coli, Bacillus subtilis, Brevibacillus, Staphylococcus, Streptococcus, Streptomyces* and *Corynebacterium* may be used in terms of mass production in a low cost.

The modified Fab region-binding peptide of one or more embodiments of the present invention can be produced by cultivating the above-described transformant in a medium, allowing the transformant to express and accumulate the peptide of one or more embodiments of the present invention in the cultivated cell (including the periplasmic space of the cell) or in the culture medium (outside the cell), and collecting the desired peptide from the culture. Further, the peptide of one or more embodiments of the present invention can also be produced by cultivating the above-described transformant in a medium, allowing the transformant to express and accumulate the fusion protein containing the peptide of one or more embodiments of the present invention in the cultivated cell (including the periplasmic space of the cell) or in the culture medium (outside the cell), collecting the fusion peptide from the culture, cleaving the fusion peptide with a suitable protease, and collecting the desired peptide.

The transformant of one or more embodiments of the present invention can be cultivated in a medium in accordance with a common method for cultivating a host cell. The medium used for cultivating the obtained transformant is not particularly restricted as long as the medium enables high yield production of one or more embodiments of the present invention peptide with high efficiency. Specifically, carbon source and nitrogen source, such as glucose, sucrose, glycerol, polypeptone, meat extract, yeast extract and casamino acid can be used. In addition, an inorganic salt such as potassium salt, sodium salt, phosphate, magnesium salt, manganese salt, zinc salt and iron salt is added as required. In the case of an auxotrophic host cell, a nutritional substance necessary for the growth thereof may be added. In addition, an antibiotic such as penicillin, erythromycin, chloramphenicol and neomycin may be added as required.

Furthermore, in order to inhibit the degradation of the target peptide caused by a host-derived protease present inside or outside the transformant, a publicly-known protease inhibitor and/or other commercially available protease inhibitor may be added in an appropriate concentration. The publicly-known protease inhibitor is exemplified by phenylmethane sulfonyl fluoride (PMSF), benzamidine, 4-(2-aminoethyl)-benzenesulfonyl fluoride (AEBSF), antipain, chymostatin, leupeptin, Pepstatin A, phosphoramidon, aprotinin and ethylenediaminetetraacetic acid (EDTA).

In order to obtain rightly folded modified Fab region-binding peptide of one or more embodiments of the present invention, for example, a molecular chaperone such as GroEL/ES, Hsp70/DnaK, Hsp90 and Hsp104/ClpB may be used. For example, such a molecular chaperone is co-existed with the peptide by coexpression or as a fusion protein. As a method for obtaining rightly folded peptide, addition of an additive for assisting right folding into the medium and cultivating at a low temperature are exemplified, but the method is not restricted thereto.

The medium for cultivating transformant produced from an *Escherichia coli* as a host is exemplified by LB medium containing triptone 1%, yeast extract 0.5% and NaCl 1%, 2×YT medium containing triptone 1.6%, yeast extract 1.0% and NaCl 0.5%, or the like. For example, the transformant may be aerobically cultivated in an aeration-stirring condition at a temperature of 15 to 42° C., or 20 to 37° C., for from several hours to several days. As a result, the peptide of one or more embodiments of the present invention is accumulated in the cultivated cell (including the periplasmic space of the cell) or in the culture liquid (outside the cell) to be recovered. In some cases, the cultivating may be performed anaerobically without aeration. In the case where a recombinant peptide is secreted, the produced recombinant peptide can be recovered after the cultivation period by separating the supernatant containing the secreted peptide using a common separation method such as centrifugation and filtration from the cultivated cell. In addition, in the case where the peptide is accumulated in the cultivated cell (including the periplasmic space), the peptide accumulated in the cell can be recovered, for example, by collecting the bacterial cell from the culture liquid by centrifugation, filtration or the like, and then disrupting the bacterial cell by sonication method, French press method or the like, and/or solubilizing the bacterial cell by adding a surfactant or the like.

A method for purifying one or more embodiments of the present invention peptide can be carried out by any one or an appropriate combination of techniques such as affinity chromatography, cation or anion exchange chromatography, gel filtration chromatography and the like. It can be confirmed whether the obtained purified substance is the target peptide or not by an ordinary method such as SDS polyacrylamide gel electrophoresis, N-terminal amino acid sequence analysis and Western blot analysis.

EXAMPLES

Hereinafter, one or more embodiments of the present invention are described in more detail with Examples. However, one or more embodiments of the present invention are not restricted to the following Examples.

The modified peptide obtained in the following Examples is described as "domain-introduced mutation", and a peptide into which mutation is not introduced is described as "domain-Cont". For example, a modified SpG-β1 (SpG-β1#) of which amino acid sequence is SEQ ID NO: 1 and of which binding capability to Fab is improved is described as "GB1#-Cont", and a modified SpG-β1 having an amino acid sequence of SEQ ID NO: 1 into which a mutation to substitute Thr at the 17$^{th}$ position by Ala (T17A) is introduced is described as "GB1#-T17A". With respect to a mutant into which two kinds of mutations are simultaneously introduced, the mutations are written together with using a slash. For example, a modified SpG-β1# into which mutations of T17A and D36V are introduced is described as "GB1#-T17A/D36V".

With respect to a peptide formed by connecting a plurality of single domains, the number of domain is put down with "d" after a period. For example, a peptide formed by connecting two modified SpG-β1# into which mutations of T17A and D36V are introduced is described as "GB1#-T17A/D36V.2d". In addition, when Cys residue (C) having a functional group for immobilization is added to the C-terminal to immobilize the peptide on a water-insoluble carrier, a single character code of an added amino acid is described after "d". For example, a peptide formed by connecting two modified SpG-β1# into which mutations of T17A and D36V are introduced and by adding Cys to the C-terminal is described as "GB1#-T17A/D36V.2dC".

Example 1

Preparation of Various Modified SpG-β1#

(1) Preparation of Expression Plasmids of Various Modified SpG-β1#

Expression plasmids of various modified SpG-β1# were prepared by using an expression plasmid of GB1#-Cont.1d as a template plasmid and introducing a mutation into the expression plasmid. The above GB1#-Cont.1d is a peptide before the introduction of a substitution mutation as Comparative example.

Figure 1:
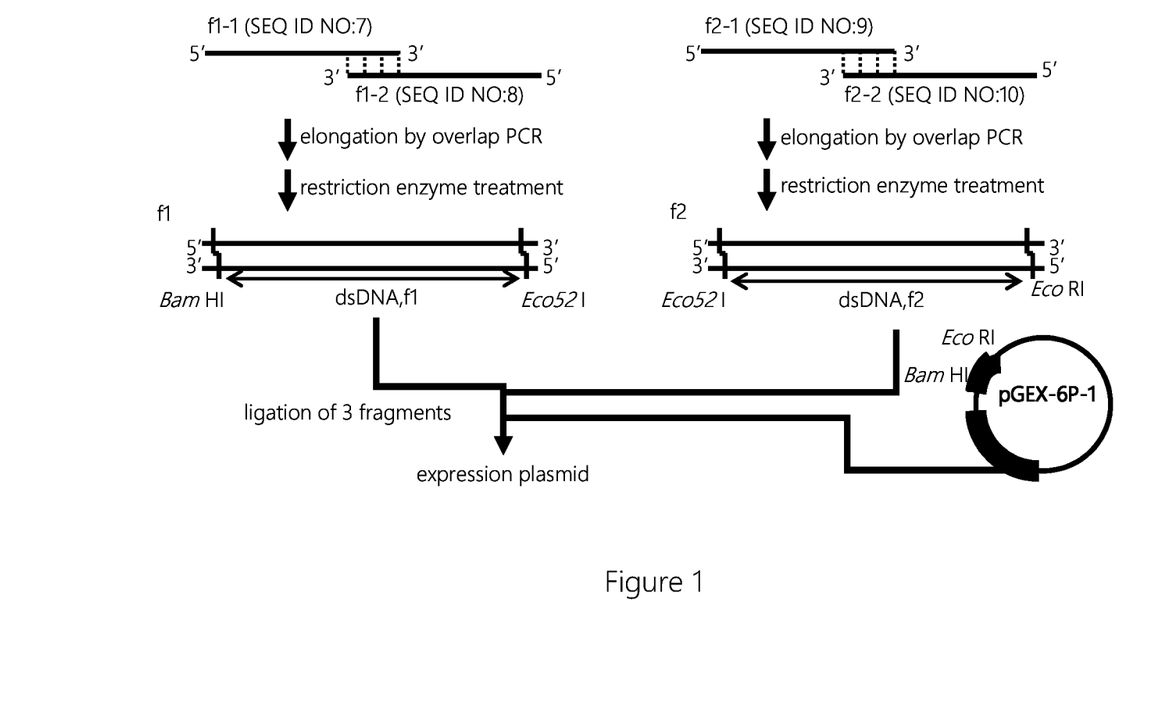
FIG. 1 represents a method for preparing an expression plasmid of GB1#-Cont.1d (SEQ ID NO: 1).

First, a base sequence of SEQ ID NO: 6 encoding GB1#-Cont.1d was designed by reverse translation from the amino acid sequence of SEQ ID NO: 1 of the peptide. Then, the code DNA was prepared and inserted into a vector for expression in accordance with the method represented in FIG. 1. A DNA encoding GB1#-T17A.1d was prepared by ligating two kinds of double-stranded DNAs (f1 and f2) having the same restriction enzyme site, and integrated into the multiple cloning site of an expression vector. In fact, the preparation of the peptide-coding DNA and the integration into the vector were simultaneously performed by ligating three fragments for connecting three double-stranded DNAs of the two kinds of double-stranded DNAs and an expression vector. The two kinds of double-stranded DNAs were prepared by elongating two kinds of single-stranded DNAs (f1-1/f1-2 or f2-1/f2-2) respectively containing about 30-base complementary region with overlapping PCR. Hereinafter, the specific experimental procedure is described. Single-stranded oligo DNAs f1-1 (SEQ ID NO: 7)/f1-2 (SEQ ID NO: 8) were synthesized by outsourcing to Sigma Genosys. The overlapping PCR was performed using Blend Taq (TOYOBO CO., LTD.) as a polymerase. The PCR product was subjected to agarose electrophoresis and the target band was cut out to extract the double-stranded DNA. The thus extracted double-stranded DNA was cleaved with the restriction enzymes BamHI and Eco52I (both available from Takara Bio, Inc.). Similarly, single-stranded oligo DNAs f2-1 (SEQ ID NO: 9)/f2-2 (SEQ ID NO: 10) were synthesized by outsourcing. The double-stranded DNA synthesized by overlapping PCR was extracted and cleaved with the restriction enzymes Eco52I and EcoRI (both available from Takara Bio, Inc.). Then, the two kinds of double-stranded DNAs were sub-cloned into the BamHI/EcoRI site in the multiple cloning site of a plasmid vector pGEX-6P-1 (GE Healthcare Bioscience). The ligation reaction for the subcloning was performed using Ligation high (TOYOBO CO., LTD.) in accordance with the protocol attached to the product.

A competent cell ("Escherichia coli HB101" manufactured by Takara Bio, Inc.) was transformed using the above-described plasmid vector pGEX-6P-1 in accordance with the protocol attached to the competent cell product. By using the plasmid vector pGEX-6P-1, GB1#-Cont.1d which was fused with glutathione-S-transferase (hereinafter, abbreviated as "GST") could be produced. Then, the plasmid DNA was amplified and extracted using a plasmid purification kit ("Wizard Plus SV Minipreps DNA Purification System" manufactured by Promega) in accordance with the standard protocol attached to the kit. The base sequence of the peptide-coding DNA of the expression plasmid was determined by using a DNA sequencer ("3130xl Genetic Analyzer" manufactured by Applied Biosystems). The sequencing PCR was performed by using a gene analysis kit ("BigDye Terminator v.1.1 Cycle Sequencing Kit" manufactured by Applied Biosystems) and DNA primers for sequencing the plasmid vector pGEX-6P-1 (manufactured by GE Healthcare Bioscience) in accordance with the attached protocol. The sequencing product was purified by using a plasmid purification kit ("BigDye XTerminator Purification Kit" manufactured by Applied Biosystems) in accordance with the attached protocol and used for the base sequence analysis.

The DNAs encoding various modified SpG-β1# were prepared by different methods depending on whether a mutation was introduced at the $17^{th}$ position or the $36^{th}$ position. When a mutation is introduced at the $17^{th}$ position, a double-stranded DNA which could be inserted in pGEX-6P by using a restriction enzyme was prepared by PCR using the above-described expression vector of GB1#-Cont.1d as a template, DNA primers of SEQ ID NOs: 11 and 12, and 3'-side DNA primer for pGEX-6P-1 sequencing. The PCR was conducted using Blend Taq-Plus- (TOYOBO CO., LTD.) in accordance with the enclosed protocol. The double-stranded DNA was cleaved using restriction enzymes BamHI and EcoRI, and ligated to the BamHI/EcoRI site of pGEX-6P-1 similarly to the above-described procedure to prepare an expression vector of various modified SpG-β1# which was mutated at the $17^{th}$ position. When a mutation is introduced at the $36^{th}$ position, a double-stranded DNA which corresponded to f2 of FIG. 1 by similar PCR using a DNA primer of SEQ ID NO: 13 and 3'-side DNA primer for pGEX-6P-1 sequencing. The double-stranded DNA and an expression plasmid of GB#1-Cont.1d were cleaved using restriction enzymes Eco52I and EcoRI, and ligated similarly to the above-described procedure to prepare an expression vector of various modified SpG-β1# which was mutated at the $36^{th}$ position. A transformation and base sequence analysis were performed in a similar manner described above. The SEQ ID NO of the base sequence of a DNA primer used for preparing each mutant, base sequence of cDNA encoding the mutant and the amino acid sequence of the mutant are shown in Table 1.

TABLE 1

| Mutant | Primer DNA | Code DNA | Amino acid |
|---|---|---|---|
| GB1#-T17A.1d | SEQ ID NO: 11 | SEQ ID NO: 14 | SEQ ID NO: 17 |
| GB1#-T17V.1d | SEQ ID NO: 12 | SEQ ID NO: 15 | SEQ ID NO: 18 |
| GB1#-D36V.1d | SEQ ID NO: 13 | SEQ ID NO: 16 | SEQ ID NO: 19 |

(2) Preparation of Various Modified SpG-β1#

The transformant produced by integrating each of modified SpG-β1# gene obtained in the above-described (1) was cultivated in 2×YT medium containing ampicillin at 37° C. overnight. The culture liquid was inoculated in 2×YT medium containing about 100-fold amount of ampicillin for cultivation at 37° C. for about 1 hour and then at 25° C. for about 1 hour. Next, isopropyl-1-thio-β-D-galactoside (IPTG) was added so that the final concentration thereof became 0.1 mM, and the transformant was further cultivated at 25° C. for about 18 hours.

After the cultivation, the bacterial cell was collected by centrifugation and re-suspended in 5 mL of PBS buffer. The cell was broken by sonication and centrifuged to separate a supernatant fraction as a cell-free extract and an insoluble fraction. When a target gene is integrated into the multiple cloning site of pGEX-6P-1 vector, a fusion peptide having GST added to the N-terminal is produced. Each fraction was analyzed by SDS electrophoresis; as a result, a peptide band assumed to be induced by IPTG was detected at a position corresponding to a molecular weight of about 25,000 or more in the cases of each of all the cell-free extracts obtained from all of the culture liquids of each transformant. The positions were different depending on the kind of a mutant, though the molecular weights were approximately similar.

The GST fusion peptide was roughly purified from each of the cell-free extract containing the GST fusion peptide by affinity chromatography using a GSTrap FF column (GE Healthcare Bioscience), which had an affinity for GST. Specifically, each of the cell-free extract was added to the GSTrap FF column and the column was washed with a standard buffer (20 mM $NaH_2PO_4$—$Na_2HPO_4$, 150 mM. NaCl, pH 7.4). Then, the target GST fusion peptide was eluted by using an elution buffer (50 mM Tris-HCl, 20 mM Glutathione, pH 8.0). When the peptide was subjected to an assay as fused with GST in the following Examples, the eluate was concentrated using Amicon (manufactured by Merck Millipore), the elution buffer was replaced by the standard buffer, and the obtained peptide solution was used.

When a gene is integrated into the multiple cloning site of pGEX-6P-1 vector, an amino acid sequence by which GST can be cleaved using sequence-specific protease: PreScission Protease (GE Healthcare Bioscience) is inserted between GST and a target protein. By using such PreScission Protease, GST was cleaved in accordance with the attached protocol. The target peptide was purified by gel filtration chromatography using a Superdex 75 10/300 GL column (GE Healthcare Bioscience) from the GST-cleaved sample used for assay. Each of the reaction mixture was added to the Superdex 75 10/300 GL column equilibrated with the standard buffer, and the target peptide therein was separated and purified from the cleaved GST and PreScission Protease. The above-described all of the peptide purification by chromatography using the column were performed by using AKTAprime plus system (GE Healthcare Bioscience). In addition, after the cleavage of GST, the sequence of Gly-Pro-Leu-Gly-Ser (SEQ ID NO: 20) derived from the vector pGEX-6P-1 was added at the N-terminal side of the peptide produced in the present Example.

Example 2

Evaluation of Affinity of Various Modified SpG-β1# for aTNF-Fab (1) Preparation of Fab Fragment A humanized monoclonal IgG product as a raw material was fragmented into a Fab fragment and a Fc fragment using papain, and only the Fab fragment was separated and purified. Specifically, anti-human TNFα monoclonal IgG (generic name: "Infliximab", product name: "Remicade" manufactured by Mitsubishi Tanabe Pharma Corporation) was dissolved in a buffer for papain treatment (0.1 M AcOH—AcONa, 2 mM EDTA, 1 mM cysteine, pH 5.5), and agarose on which papain was immobilized ("Papain Agarose from papaya latex" manufactured by SIGMA) was added thereto. The mixture was incubated with stirring by a rotator at 37° C. for about 8 hours. The IgG-Fab was purified by recovering as a flow-through fraction in an affinity chromatography using MabSelect SuRe column (GE Healthcare Bioscience) from the reaction mixture which contained both of a Fab fragment and a Fc fragment and which was separated from the agarose on which papain was immobilized. The obtained IgG-Fab solution was subjected to purification by gel filtration chromatography using Superdex 75 10/300 GL column to obtain the solution of IgG-Fab (aTNF-Fab). In the chromatography, the standard buffer was used for equilibration and separation. Similarly to the above-described Example 1, AKTAprime plus system was used in the chromatography for peptide purification.

(2) Analysis of Affinity of Various Modified SpG-β1# for Fab

The affinity of each various modified SpG-β1# obtained in the above Example 1(2) for aTNF-Fab was evaluated using a biosensor Biacore 3000 (GE Healthcare Bioscience) utilizing surface plasmon resonance. In the present Example, the aTNF-Fab obtained in the above Example 2(1) was immobilized on a sensor tip, and each of the peptide was flown on the tip to detect the interaction between the two. The aTNF-Fab was immobilized on a sensor tip CM5 by amine coupling method using N-hydroxysuccinimide (NHS) and N-ethyl-N'-(3-dimethylaminopropyl)carbodiimide hydrochloride (EDC), and ethanolamine was used for blocking. All of the sensor tip and reagents for immobilization were manufactured by GE Healthcare Bioscience. The aTNF-Fab solution was diluted about 10 times using a buffer for immobilization (10 mM AcOH—AcONa, pH 4.5), and the aTNF-Fab was immobilized on the sensor tip in accordance with the protocol attached to the Biacore 3000. In addition, a reference cell as negative control was also prepared by activating another flow cell on the tip with EDC/NHS, immobilizing nothing and blocking with ethanolamine. Peptide solutions of each various modified SpG-β1# having concentrations of 0.01, 0.1, 1 or 10 μM were prepared using a running buffer (20 mM $NaH_2PO_4$—$Na_2HPO_4$, 150 mM NaCl, 0.005% P-20, pH 7.4). The peptide solution was added to the sensor tip in a flow rate of 40 μL/min for 1 minute. Bonding response curves at the time of addition (association phase, for 1 minute) and after the addition (dissociation phase, for 1 minute) were sequentially obtained at a measurement temperature of 25° C. After each measurement, the cells were washed using about 20 mM NaOH. The bonding response curve obtained by subtracting the bonding response curve of the reference cell was subjected to fitting analysis by a binding model of 1:1 using a software BIA evaluation attached to the system, and affinity constant ($K_A = k_{on}/k_{off}$) to aTNF-Fab was calculated. The result is shown in Table 2 with each binding parameter of GB1#-Cont.1d, which parameter was measured in Comparative Example 2.

TABLE 2

| | $k_{on}$ ($\times 10^4$ [$M^{-1}s$]) | $k_{off}$ ($\times 10^{-2}$ [$s^{-1}$]) | $K_A$ ($\times 10^6$ [$M^{-1}$]) |
|---|---|---|---|
| GB1#-Cont.1d | 4.17 | 1.70 | 2.45 |
| GB1#-T17A.1d | 2.50 | 2.85 | 0.88 |
| GB1#-T17V.1d | 1.91 | 3.35 | 0.57 |
| GB1#-D36V.1d | 3.28 | 6.40 | 0.51 |

As the result shown in Table 2, the values of affinity constant $K_A$ of the mutants in which a mutation of T17A, T17V or D36V was introduced for a TNF-Fab were lower than the $K_A$ value of SpG-β1# (GB1#-Cont.1d) before the introduction of the mutation. It was not confirmed that the binding capability was significantly decreased down to 1/10 or less, as the value was 5×10⁵ (1/M) or more. A binding capability to Fab is sufficient as long as a ligand in a column can adsorb the Fab as a target molecule. When a binding capability to Fab is too high, the Fab may not possibly be eluted. A ligand having a binding capability of 5×10⁵ (1/M) or more can be therefore considered to properly function.

Example 3

Measurement of Acid Dissociation pH Between Various Modified SpG-β1# and aTNF-Fab (1) Preparation of Fab Fragment-Immobilized Carrier An affinity separation matrix on which aTNF-Fab obtained in the above Example 2 was immobilized was prepared by using a commercially available coupling column for immobilizing a ligand. The column has an amino group as a functional group for coupling.

As a water-insoluble carrier, 1 mL of a commercially available prepacked column ("Hitrap NHS activated HP" manufactured by GE Healthcare Bioscience) was used. The column contains a crosslinked agarose as a base material and an amino group is introduced as an active functional group for immobilizing a protein ligand, and a ligand was immobilized in accordance with the product manual. Specifically, 2 mL of ice-cooled 1 mM HCl was flown at a rate of 1 mL/min repeatedly three times to remove isopropanol in the column.

Then, 1 mL of a 1 mg/mL aTNF-Fab solution in a coupling buffer (0.2 MNaHCO₃, 0.5 MNaCl, pH 8.3) was immediately flown at the same rate. The top and bottom of the column were stoppled, and the column was stood still at 25° C. for 30 minutes to immobilize the obtained ligand on the column.

Then, the column was opened, and 3 mL of the coupling buffer was flown at the same rate to recover the unreacted aTNF-Fab. Next, 2 mL of a blocking buffer (0.5 M ethanolamine, 0.5 M NaCl, pH 8.3) was flown repeatedly three times and 2 mL of a washing buffer (0.1 M acetic acid, 0.5 M NaCl, pH 4.0) was flown three times. Each of the above-described procedure to flow the blocking buffer and washing buffer were performed three times one after the other. Finally, 2 mL of a standard buffer (20 mM NaH₂PO₄—Na₂HPO₄, 150 mM NaCl, pH 7.4) was flown to complete the preparation of an affinity separation matrix.

(2) Chromatography Experiment Using Fab Fragment-Immobilized Carrier

By affinity purification chromatography using aTNF-Fab-immobilized column prepared in Example 3(1), an acid dissociation pH at which each modified SpG-β1# prepared in Example 1 (2) was eluted and which corresponded to the peak top of an elution curve of the modified SpG-β1# was measured. Specifically, AKTAprime plus system was used as a chromatography system. The column was equilibrated using ion exchange buffer A (50 mM citric acid-citrate Na, pH 5.5). Into the column, 0.1 mL of a protein solution containing each modified SpG-β1# in the concentration of about 0.1 mg/mL was added, and the protein was eluted with the pH linear gradient from pH 5.5 to pH 2.5. More specifically, the ion exchange buffer A and ion exchange buffer B (50 mM AcOH—AcONa, 1 M NaCl, pH 2.5) were used. While 20 column volume of the buffer was flown through the column, the concentration of the buffer B was linearly increased from 0% to 100% to identify an acid dissociation pH on the basis of an elution position. The pH value which was specified in the experiment as the value corresponding to each elution peak top is shown in Table 3 in addition to the result of Comparative example 3.

TABLE 3

|  | Dissociation pH |
| --- | --- |
| GB1#-Cont.1d | 2.60 |
| GB1#-T17A.1d | 2.85 |
| GB1#-T17V.1d | 3.00 |
| GB1#-D36V.1d | 3.40 |

Figure 2:
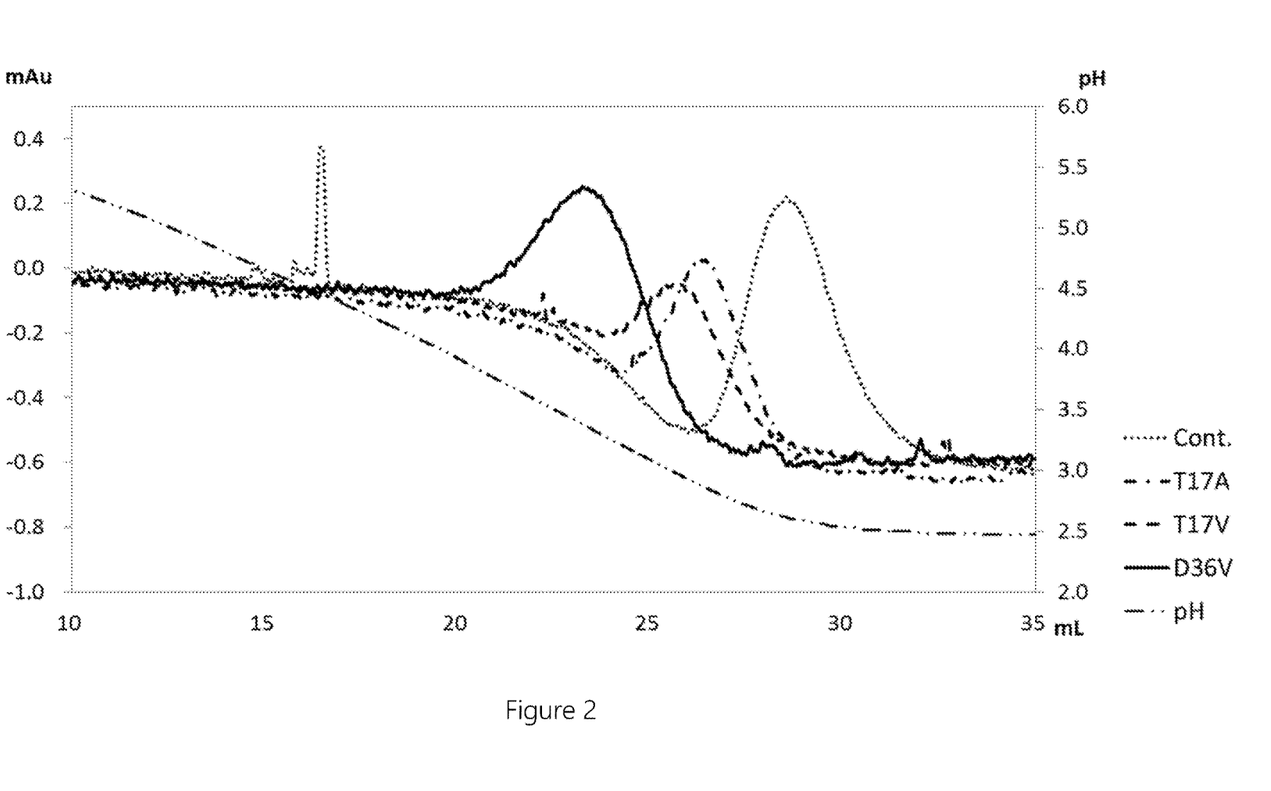
FIG. 2 are charts of affinity chromatography when various modified SpG-β1# were added to aTNF-Fab-immobilized carrier and were eluted by pH gradient.

In addition, chromatography charts with respect to various modified SpG-β1# are shown as FIG. 2 so that the charts can be compared with that of SpG-β1# before the introduction of a mutation of Comparative example 3.

As the result shown in Table 3 and FIG. 2, the various modified SpG-β1# such as GB1#-T17A.1d, GB1#-T17V.1d and GB1#-D36V.1d obtained by the present invention were eluted earlier than GB1#-Cont.1d without a mutation. This result indicates that the various modified SpG-β1# are eluted by pH closer to neutral side. In other words, the result indicates that the pH to dissociate a Fab region-containing protein from one or more embodiments of the present invention peptide is improved to closer to neutrality. In addition, the result of the present Example suggests that the binding capability of one or more embodiments of the present invention peptide to Fab is so strong at pH 5.5 that the Fab can be held on the carrier, and it is contemplated that one or more embodiments of the present invention peptide on which Fab is held can be subjected to an intermediate washing at and around the pH.

Comparative Example 1

Preparation of GB1#-Cont.1d (SpG-β1#)

Similarly to the procedure of Example 1, a transformant was prepared using the expression vector of GB1#-Cont.1d prepared in Example 1, and a solution of GB1#-Cont.1d was prepared by way of cultivation and purification.

Comparative Example 2

Evaluation of Affinity of GB1#-Cont.1d for aTNF-Fab

An affinity of GB1#-Cont.1d prepared in Comparative example 1 for aTNF-Fab prepared in Example 2(1) was evaluated similarly to the procedure of Example 2(2). The result is shown in the above Table 2.

Comparative Example 3

Measurement of Acid Dissociation pH Between GB1#-Cont.1d and aTNF-Fab

An acid dissociation pH of GB1#-Cont.1d prepared in Comparative example 1 was measured using aTNF-Fab-immobilized carrier prepared in Example 3(1) similarly to the procedure of Example 3(2). The result is shown in the above Table 3.

Although embodiments of the disclosure have been described using specific terms, devices, and methods, such description is for illustrative purposes only. The words used are words of description rather than limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the preferred versions contained therein.

What is claimed is:

1. A modified IgG Fab region-binding peptide, comprising an amino acid sequence of SEQ ID NO: 1 with one or two substitutions,
   wherein the one or two substitutions are selected from the group consisting of: a substitution of Thr at the 17$^{th}$ position by Ala, Val, Ser, or Leu; and a substitution of Asp at the 36$^{th}$ position by Ala, Val, or Thr,
   wherein an acid dissociation pH of the modified IgG Fab region-binding peptide is shifted to a neutral side relative to an acid dissociation pH of an IgG Fab region-binding peptide comprising the amino acid sequence SEQ ID NO: 1 without the one or two substitutions.

2. The modified IgG Fab region-binding peptide according to claim 1, wherein the one or two substitutions are selected from the group consisting of: a substitution of Thr at the 17$^{th}$ position by Ala or Val; and a substitution of Asp at the 36$^{th}$ position by Val.

3. The modified IgG Fab region-binding peptide according to claim 1, comprising an amino acid sequence selected from the group consisting of SEQ ID NOs: 17 to 19.

4. An affinity separation matrix, wherein the modified IgG Fab region-binding peptide according to claim 1 is immobilized on a water-insoluble carrier as a ligand.

5. A modified IgG Fab region-binding peptide multimer, comprising two or more domains formed by connecting two or more of the modified IgG Fab region-binding peptides according to claim 1.

6. An affinity separation matrix, wherein the modified IgG Fab region-binding peptide multimer according to claim 5 is immobilized on a water-insoluble carrier as a ligand.

* * * * *